(12) United States Patent
D'Ambrosio et al.

(10) Patent No.: US 9,875,461 B2
(45) Date of Patent: *Jan. 23, 2018

(54) STORAGE CABINET WITH MULTIPLE RFID READERS

(71) Applicant: Omnicell, Inc., Mountain View, CA (US)

(72) Inventors: George John D'Ambrosio, Mountain View, CA (US); Onne Ganel, Mountain View, CA (US); Nat Moody, Mountain View, CA (US); Gerardo Moreno, Mountain View, CA (US)

(73) Assignee: Omnicell, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,023

(22) Filed: Apr. 4, 2016

(65) Prior Publication Data

US 2017/0053230 A1 Feb. 23, 2017

Related U.S. Application Data

(63) Continuation of application No. 14/084,349, filed on Nov. 19, 2013, now Pat. No. 9,324,051.

(Continued)

(51) Int. Cl.
*G06K 19/00* (2006.01)
*G06Q 10/08* (2012.01)
(Continued)

(52) U.S. Cl.
CPC ....... *G06Q 10/087* (2013.01); *G06K 7/10297* (2013.01); *G06K 7/10366* (2013.01);
(Continued)

(58) Field of Classification Search
USPC .......................... 235/487, 492; 340/10, 572
See application file for complete search history.

(56) References Cited

U.S. PATENT DOCUMENTS

| 4,227,037 A | 10/1980 | Layton |
| 4,496,406 A | 1/1985 | Dedow |

(Continued)

FOREIGN PATENT DOCUMENTS

| CN | 202443479 U | 9/2012 |
| CN | 105122324 A | 12/2015 |

(Continued)

OTHER PUBLICATIONS

U.S. Appl. No. 14/084,349, "Advisory Action", dated May 11, 2015, 3 pages.

(Continued)

*Primary Examiner* — Matthew Mikels
(74) *Attorney, Agent, or Firm* — Kilpatrick Townsend & Stockton LLP

(57) ABSTRACT

An RFID cabinet system is provided for monitoring items having an RFID tag. System includes cabinet having open interior where items are stored and at least one door providing access to items. Static RFID system is provided for reading and identifying data embedded on RFID tag located on at least some of the items placed within cabinet. Static RFID system is configured to monitor substantially all items located within the interior of cabinet when door is closed. Transaction RFID system is provided for reading one of the RFID tags upon removal or return of the associated item from cabinet. Transaction RFID system is operable when door is open. Computer system is configured to sense opening and closing of door. Computer system is configured to receive input that identifies user, and computer system is (Continued)

configured to periodically record data read from RFID tags by static RFID system and transaction RFID system.

20 Claims, 2 Drawing Sheets

Related U.S. Application Data

(60) Provisional application No. 61/727,956, filed on Nov. 19, 2012.

(51) Int. Cl.
*G06Q 50/22* (2012.01)
*G06K 7/10* (2006.01)
*G06K 7/14* (2006.01)
*G07C 9/00* (2006.01)

(52) U.S. Cl.
CPC ............ *G06K 7/1413* (2013.01); *G06Q 50/22* (2013.01); *G07C 9/00158* (2013.01); *G07C 9/00912* (2013.01)

(56) References Cited

U.S. PATENT DOCUMENTS

| | | | |
|---|---|---|---|
| 5,190,185 A | 3/1993 | Blechl | |
| 5,377,864 A | 1/1995 | Blechl et al. | |
| 5,385,505 A | 1/1995 | Sharp et al. | |
| 5,739,765 A | 4/1998 | Stanfield et al. | |
| 5,745,366 A | 4/1998 | Higham et al. | |
| 5,751,221 A | 5/1998 | Stanfield et al. | |
| 5,771,003 A | 6/1998 | Seymour | |
| 5,774,053 A | 6/1998 | Porter | |
| 5,774,059 A | 6/1998 | Henry et al. | |
| 5,805,455 A | 8/1998 | Lipps | |
| 5,805,456 A | 9/1998 | Higham et al. | |
| 5,905,653 A | 5/1999 | Higham et al. | |
| 5,927,540 A | 7/1999 | Godlewski | |
| 5,936,527 A | 8/1999 | Isaacman et al. | |
| 6,011,999 A | 1/2000 | Holmes | |
| 6,039,467 A | 3/2000 | Holmes | |
| 6,127,928 A | 10/2000 | Issacman et al. | |
| 6,151,536 A | 11/2000 | Arnold et al. | |
| 6,170,929 B1 | 1/2001 | Wilson et al. | |
| 6,204,764 B1 | 3/2001 | Maloney | |
| 6,204,784 B1 | 3/2001 | Hatfield | |
| 6,219,587 B1 | 4/2001 | Ahlin et al. | |
| 6,272,394 B1 | 8/2001 | Lipps | |
| 6,327,576 B1 | 12/2001 | Ogasawara | |
| 6,354,783 B1 | 3/2002 | Stoy et al. | |
| 6,385,505 B1 | 5/2002 | Lipps | |
| 6,407,665 B2 | 6/2002 | Maloney | |
| 6,435,370 B1 | 8/2002 | Wilson | |
| 6,512,459 B2 | 1/2003 | Benezech et al. | |
| 6,604,019 B2 | 8/2003 | Ahlin et al. | |
| 6,609,047 B1 | 8/2003 | Lipps | |
| 6,640,159 B2 | 10/2003 | Holmes et al. | |
| 6,677,857 B2 | 1/2004 | Bara et al. | |
| 6,693,539 B2 | 2/2004 | Bowers et al. | |
| 6,703,935 B1 | 3/2004 | Chung et al. | |
| 6,707,381 B1 | 3/2004 | Maloney | |
| 6,760,643 B2 | 7/2004 | Lipps | |
| 6,975,922 B2 | 12/2005 | Duncan et al. | |
| 6,989,749 B2 | 1/2006 | Mohr | |
| 7,072,855 B1 | 7/2006 | Godlewski et al. | |
| 7,100,792 B2 | 9/2006 | Hunter et al. | |
| 7,218,231 B2 | 5/2007 | Higham | |
| D547,519 S | 7/2007 | Reckelhoff | |
| 7,249,688 B2 | 7/2007 | Hunter et al. | |
| D549,921 S | 8/2007 | Reckelhoff | |
| 7,348,884 B2 | 3/2008 | Higham | |
| 7,554,449 B2 | 6/2009 | Higham | |
| 7,571,024 B2 | 8/2009 | Duncan et al. | |
| 7,588,167 B2 | 9/2009 | Hunter et al. | |
| 7,675,421 B2 | 3/2010 | Higham | |
| 7,734,369 B2 | 6/2010 | Godlewski et al. | |
| 7,835,819 B2 | 11/2010 | Duncan et al. | |
| 7,979,310 B2 | 7/2011 | Pujar et al. | |
| 8,027,749 B2 | 9/2011 | Vahlberg et al. | |
| 8,073,563 B2 | 12/2011 | Vahlberg et al. | |
| 8,126,590 B2 | 2/2012 | Vahlberg et al. | |
| 8,131,397 B2 | 3/2012 | Vahlberg et al. | |
| 8,140,186 B2 | 3/2012 | Vahlberg et al. | |
| 8,155,786 B2 | 4/2012 | Vahlberg et al. | |
| 8,180,485 B2 | 5/2012 | Reckelhoff | |
| 8,239,062 B2 | 8/2012 | Vahlberg et al. | |
| 8,280,550 B2 | 10/2012 | Levy et al. | |
| 8,378,620 B2 | 2/2013 | Reckelhoff | |
| 8,416,080 B2 | 4/2013 | Higham | |
| 8,484,049 B2 | 7/2013 | Mullenger et al. | |
| 9,324,051 B2 * | 4/2016 | D'Ambrosio ........ G06Q 10/087 | |
| 2002/0143320 A1 | 10/2002 | Levin | |
| 2002/0145520 A1 | 10/2002 | Maloney | |
| 2002/0153411 A1 | 10/2002 | Wan et al. | |
| 2002/0190871 A1 | 12/2002 | Stanfield et al. | |
| 2003/0030539 A1 | 2/2003 | McGarry et al. | |
| 2003/0034390 A1 | 2/2003 | Linton et al. | |
| 2003/0052788 A1 | 3/2003 | Kwong-Tai Chung | |
| 2003/0117281 A1 | 6/2003 | Sriharto et al. | |
| 2003/0160698 A1 | 8/2003 | Andreasson et al. | |
| 2003/0164401 A1 | 9/2003 | Andreasson et al. | |
| 2003/0171998 A1 | 9/2003 | Pujar et al. | |
| 2003/0174099 A1 | 9/2003 | Bauer et al. | |
| 2004/0032328 A1 | 2/2004 | Rubinstein | |
| 2004/0046020 A1 | 3/2004 | Andreasson et al. | |
| 2004/0098166 A1 | 5/2004 | Spano et al. | |
| 2004/0100383 A1 | 5/2004 | Chen et al. | |
| 2004/0103033 A1 | 5/2004 | Reade et al. | |
| 2004/0113786 A1 | 6/2004 | Maloney | |
| 2004/0140884 A1 | 7/2004 | Gallagher et al. | |
| 2004/0178886 A1 | 9/2004 | Watanabe et al. | |
| 2005/0077997 A1 | 4/2005 | Landram et al. | |
| 2005/0088306 A1 | 4/2005 | Andreasson et al. | |
| 2005/0201450 A1 * | 9/2005 | Volpi .................. G06K 7/0008 375/150 | |
| 2006/0022827 A1 | 2/2006 | Higham | |
| 2006/0237427 A1 | 10/2006 | Logan | |
| 2008/0122615 A1 | 5/2008 | Shoenfeld et al. | |
| 2008/0319790 A1 | 6/2008 | Vahlberg et al. | |
| 2008/0224875 A1 | 9/2008 | Phillips et al. | |
| 2008/0319579 A1 | 12/2008 | Vahlberg et al. | |
| 2008/0319789 A1 | 12/2008 | Vahlberg et al. | |
| 2009/0021345 A1 * | 1/2009 | Sriharto ............ G08B 13/1427 340/5.6 | |
| 2010/0042437 A1 | 2/2010 | Levy et al. | |
| 2010/0079240 A1 | 4/2010 | Higham | |
| 2010/0141457 A1 * | 6/2010 | Wass .................. G06Q 10/08 340/572.8 | |
| 2010/0201494 A1 * | 8/2010 | Ryou .................. G06K 7/0008 340/10.2 | |
| 2010/0252626 A1 | 10/2010 | Elizondo et al. | |
| 2012/0019358 A1 | 1/2012 | Azevedo et al. | |
| 2012/0130534 A1 | 5/2012 | Wurm | |
| 2012/0176245 A1 | 7/2012 | Paydar et al. | |
| 2012/0203377 A1 | 8/2012 | Paydar et al. | |
| 2012/0245731 A1 | 9/2012 | Reckelhoff | |
| 2012/0283871 A1 | 11/2012 | Chai et al. | |
| 2012/0323362 A1 | 12/2012 | Paydar et al. | |
| 2013/0006415 A1 | 1/2013 | Paydar et al. | |
| 2013/0006652 A1 | 1/2013 | Vahlberg et al. | |
| 2013/0144435 A1 | 6/2013 | Czaplewski et al. | |
| 2013/0158705 A1 | 6/2013 | Levy et al. | |
| 2014/0074284 A1 | 3/2014 | Czaplewski et al. | |
| 2014/0138440 A1 | 5/2014 | D'Ambrosio et al. | |

FOREIGN PATENT DOCUMENTS

| | | |
|---|---|---|
| GB | 2419722 A | 5/2006 |
| JP | 2000154673 A | 6/2000 |
| JP | 2000310476 A | 11/2000 |
| JP | 2002193448 A | 7/2002 |
| JP | 2003298280 A | 10/2003 |

(56) References Cited

FOREIGN PATENT DOCUMENTS

| | | |
|---|---|---|
| JP | 2005046420 A | 2/2005 |
| JP | 2005108122 A | 4/2005 |
| KR | 20150087371 A | 7/2015 |
| WO | 2008035294 A2 | 3/2008 |
| WO | 2014078860 A1 | 5/2014 |

OTHER PUBLICATIONS

U.S. Appl. No. 14/084,349, "Final Office Action", dated Feb. 20, 2015, 10 pages.
U.S. Appl. No. 14/084,349, "Non-Final Office Action", dated Sep. 25, 2014, 8 pages.
U.S. Appl. No. 14/084,349, "Non-Final Office Action", dated Jul. 2, 2015, 10 pages.
U.S. Appl. No. 14/084,349, "Notice of Allowance", dated Dec. 30, 2015, 8 pages.
EP13854749.2, "Extended European Search Report", dated Mar. 31, 2016, 8 pages.
PCT/US2013/070811, "International Search Report and Written Opinion", dated Feb. 14, 2014, 8 pages.
PCT/US2013/070311 , "International Preliminary Report on Patentability", dated May 28, 2015, 7 pages.
CA 2,574,949, "Office Action", dated Oct. 3, 2008, 3 pages.
JP2007-523663, "Office Action" (with translation), dated Nov. 17, 2011, 8 pages.
KR 10-2007-7002467 "Office Action" (with translation), dated Jul. 29, 2011, 8 pages.
JP Patent Application No. 2015-543120, "Office Action", dated on Oct. 17, 2017, 9 pages (5 pages for original, 4 pages for translation).

* cited by examiner

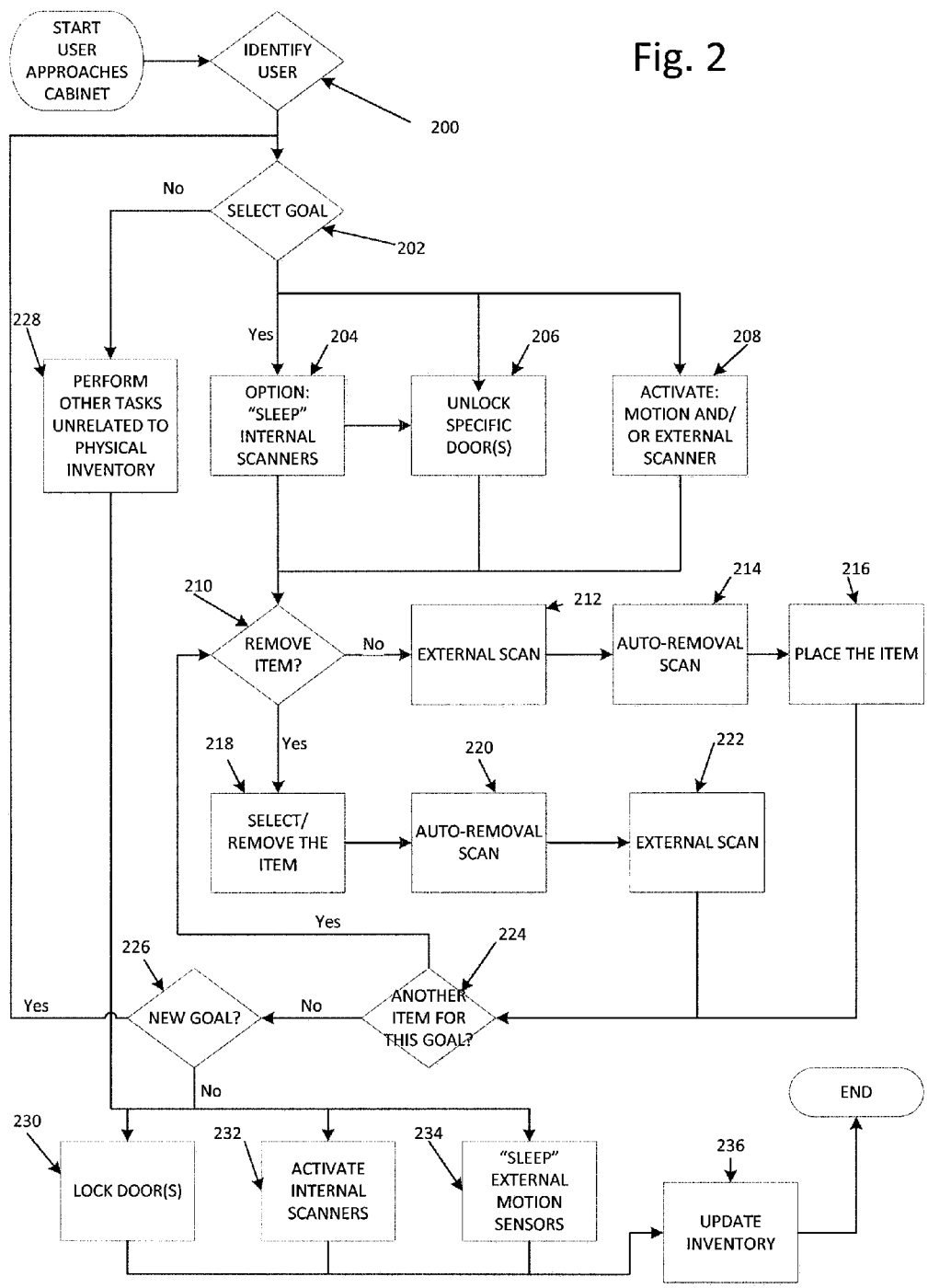

STORAGE CABINET WITH MULTIPLE RFID READERS

CROSS-REFERENCES TO RELATED APPLICATIONS

This application is a continuation of U.S. patent application Ser. No. 14/084,349, filed Nov. 19, 2013, which claims the benefit of U.S. Provisional Patent Application No. 61/727,956, filed Nov. 19, 2012, entitled "STORAGE CABINET WITH MULTIPLE RFID READERS", which is hereby incorporated by reference, as if set forth in full in this document, for all purposes.

BACKGROUND OF THE INVENTION

In the healthcare industry, the availability of supply items, including medications, is critical. Also important is the ability to keep an accurate accounting, not only of the items used, but also of their location. Tracking location and usage in real time has proved to be a difficult and challenging task.

In addition, closed cabinet systems exist that prevent the removal of items without the entry of necessary data to perform the above tracking and prevent diversion or theft. Such a system is particularly applicable to the expensive items that are used in an operating room (OR) or cath lab. However, closed cabinet systems are also applicable to the high volume diversion of inexpensive items that are useful outside the healthcare facility such as batteries, bandages, shampoos, and pens etc., where the user may consider the item too small to be considered "theft."

In developing such systems, the challenge lies in balancing convenience and speed of access along with entering the necessary data to identify the user, the product, and the account number or patient. Systems that dispense an individual product in the same manner as a candy machine, while desirable for convenience and security, are usually too expensive, require special packaging, and are not flexible in terms of the various size and configurations of product that need to be stocked in a hospital. They are also not very space efficient, since items are individually spaced and housed.

The use of RFID tabs on products presents an opportunity to track individual products without the need for expensive dispensing systems. This is particularly true of expensive product where it is worth incurring the additional expense of applying the RFID tags.

BRIEF SUMMARY OF THE INVENTION

In one embodiment, a radio frequency identification (RFID) cabinet system is provided for monitoring items having an RFID tag. The system includes a cabinet having an open interior where the items are stored. The system also includes at least one door providing access to the items. At least a first RFID system is provided for reading and identifying the data embedded on an RFID tag located on at least some of the items placed within the cabinet. The first RFID system is configured to monitor substantially all of the items located within the interior of the RFID cabinet when the door is closed. At least a second RFID system is provided for reading one or more of the RFID tags upon removal of the associated item from the RFID cabinet. The second RFID system is operable when the door is open. For example, the user may grab an item in the cabinet and remove it through the second RFID system, in essence pulling the item through a "tunnel reader" to record removal of the item. A computer system is configured to sense opening and closing of the door. The computer system is also configured to receive an input that identifies a user, and the computer system is configured to periodically record data read from the RFID tags by the first RFID system and the second RFID system.

In one aspect, embodiments of the present invention provide a cabinet system for monitoring items having an RFID tag. The system can include a cabinet having an interior where items are stored and at least one door providing access to the items. The system can also include a static RFID system for reading and identifying data embedded on RFID tags located on at least some of the items placed within the cabinet. The static RFID system is configured to scan substantially all of the items located within the interior of the cabinet when the at least one door is closed. The system also provides a transaction RFID system for reading the data on one of the RFID tags upon removal of the associated item from the RFID cabinet. The transaction RFID system is operable when the door is open. The system further includes a computer system that is configured to detect opening and closing of the at least one door. The computer system can be configured to receive an input that identifies a user. The computer system is configured to periodically record the data read from the RFID tags by the static RFID system and the transaction RFID system.

In some embodiments, the cabinet further includes a plurality of doors and the interior has a plurality of storage areas. Each of the plurality of doors controls access to a corresponding one of the plurality of storage areas. In other embodiments, each of the plurality of storage areas includes a different level of access. The transaction RFID system may be configured to read the data on one of the RFID tags for a detection time that is less than about 2 seconds. The computer system may be configured to store and correlate expiration date information with the items in the cabinet and to provide an indication of an approaching or past expiration date for each of the items. In some embodiments, the input includes one or more of a biometric identifier, a username, a password, and a signal from a wireless device assigned to the user. In other embodiments, the system can further include an external item reader. The external item reader can include at least one of a RFID scanner and a bar code reader.

In another aspect, the invention provides a method of monitoring items having an RFID tag. The method can include storing a plurality of items within an interior of an enclosure defining an access-controlled area. Access to the interior can be obtained via one or more doors and at least some of the items are coupled to an RFID tag having electronically readable identification data. The method can also include using one or more static RFID scanners, while the door is closed, to read the data on substantially all of the RFID tags located within the access-controlled area to monitor an inventory of substantially all of the items. The method further includes storing the inventory in a database and authenticating a user who is requesting access to the access-controlled area. The method can include receiving an inputted goal for an item to be placed into or removed from the access-controlled area. The method can also include scanning an RFID tag of the item, while the door is open, using one or more transaction RFID scanners as the user removes the item from or places the item into the access-controlled area. The method may also include recording the removal or placement of the item in the database.

In some embodiments, authenticating a user can include verifying one or more user inputs selected from biometric identifier, a username, a password, and a signal from a wireless device assigned to the user. Using one or more static RFID scanners can include periodically scanning substantially all of the items at a scheduled interval. In some embodiments, scanning an RFID tag is completed in less than about 2 seconds. In some embodiments, storing and correlating expiration date information with the items and providing an indication of approaching or past expiration dates for the items. The method can further include activating the one or more transaction RFID scanners when the one or more doors are open and deactivating the one or more transaction RFID scanners when the one or more doors are closed. The method may also include activating the one or more static RFID scanners when the one or more doors are closed and deactivating the one or more static RFID scanners when the one or more doors are open. The method can include determining whether a second item is needed for the goal and determining whether the user has a new goal for a new item stored within the access-controlled area. Embodiments of the invention provide that the method includes reading information from an item that is externally located relative to the access-controlled area using an external scanner.

In another aspect, the present invention provides a method of monitoring items having an RFID tag. The method includes using one or more static RFID scanners to read and identify data embedded on an RFID tag located on at least some items placed within an access-controlled area to monitor an inventory of substantially all of the items when one or more doors controlling access to the access-controlled area are closed. The method can also include storing the inventory in a database and authenticating a user of an inventory management system. The method may include unlocking the one or more doors to provide the user access to the items. The method may additionally include scanning an RFID tag of the item using one or more transaction RFID scanners as the user removes the item from the access-controlled area. The method can include locking the one or more doors to prevent the user from accessing the items and recording the removal of the item in the database.

In some embodiments, the method can also include receiving an inputted goal for an item within an access-controlled area. Embodiments of the invention provide that using one or more static RFID scanners can include periodically scanning substantially all of the items at a scheduled interval. In some embodiments, the method also includes activating the one or more transaction RFID scanners when the one or more doors are open and deactivating the one or more transaction RFID scanners when the one or more doors are closed. The method can also include activating the one or more static RFID scanners when the one or more doors are closed and deactivating the one or more static RFID scanners when the one or more doors are open.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 2 is a flow chart of a method of using a RFID cabinet inventory management system according to embodiments of the invention.

DETAILED DESCRIPTION OF THE INVENTION

Figure 1:
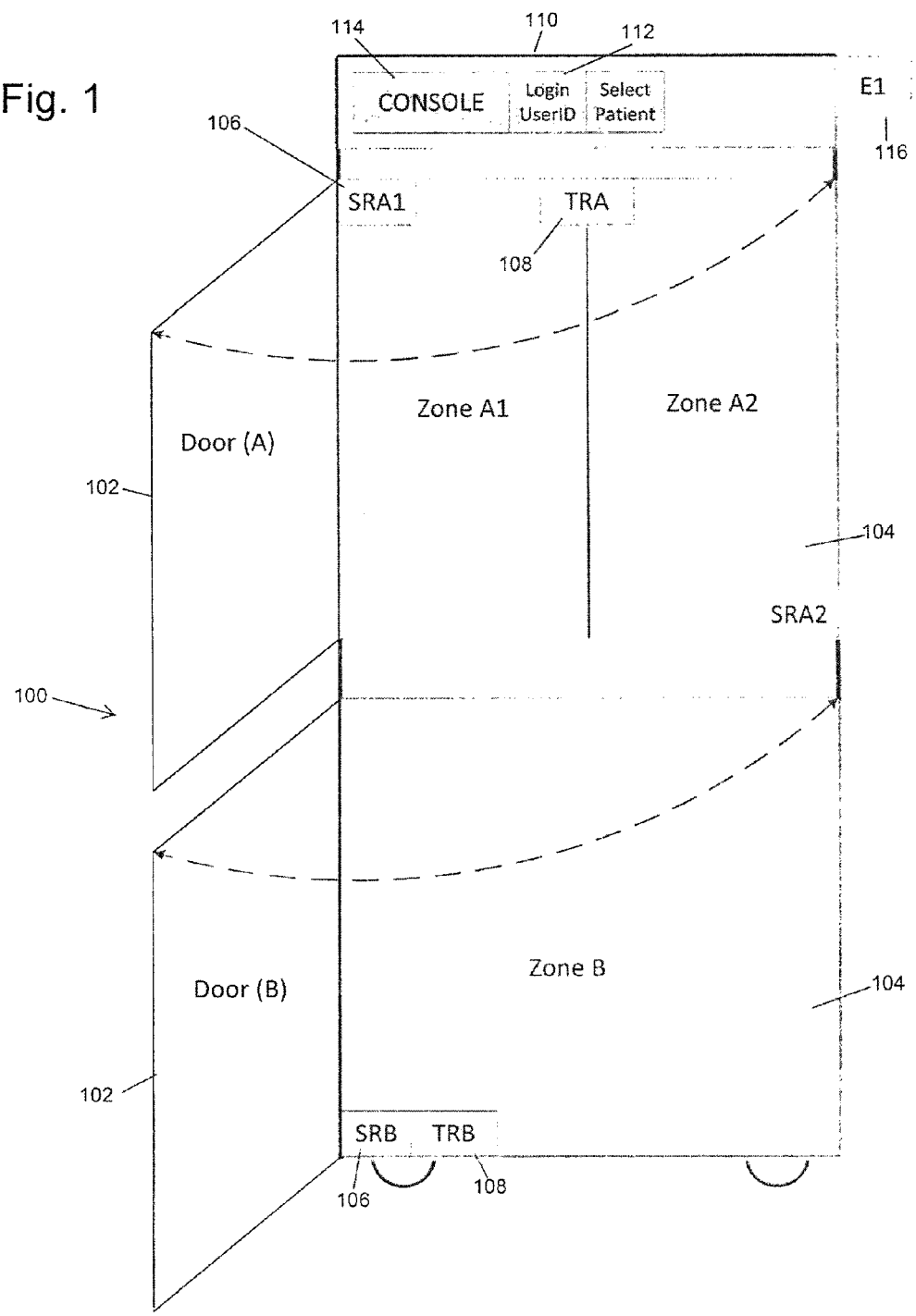
FIG. 1 illustrates a RFID cabinet inventory management system according to embodiments of the invention.

Described herein are several exemplary embodiments of the invention. Although certain features are described, for ease of discussion, in relation to certain illustrated embodiments, those skilled in the art will appreciate, based on the disclosure herein, that a variety of the inventive features can be combined in accordance with many different embodiments of the invention. The illustrated embodiments below, therefore, are provided merely by way of example and should not be considered to limit the scope of the invention, which is defined only by the appended claims.

Embodiments of the invention relate to ways to manage the workflow of items that are associated with RFID tags. This is accomplished using multiple RFID readers as described herein.

The invention takes advantage of RFID technology that is employed at point of usage locations, such as storage cabinets, carts, or locations in healthcare facilities, although the invention is not limited only to healthcare facilities. The RFID technology is used to provide automated inventory management capabilities through periodic scans of items within a cabinet or other enclosed area that is monitored by an RFID reader and antennae. Also, the RFID technology is employed to separately scan items as they are removed from the RFID cabinet or other monitored location.

One challenge experienced in configuring the RFID technology used in the invention is that, when scanning all of the items within a storage location, a delay which inconveniences the user, such as, for example, about 5-30 seconds or more, may occur. As such, a significant amount of time may pass before a determination can be made as to any missing or removed items. Ways to avoid this delay are inconvenient. Examples of such inconvenient ways to avoid this delay include waving the item in front of an external RFID scanner or barcode or manually attaching the item to the patient profile.

Accordingly, embodiments of the invention provide the ability to both scan items within the cabinet or storage location and determine when items have been removed in a minimal amount of time, usually less than 2 seconds. The system is also fully automated for the end users, eliminating the need for the end-user to wave an item in front of a scanner. This is particularly advantageous when a caregiver is removing items for multiple patients. In the process of removing (or returning) items, the caregiver may input nurse identification information and patient identification information into the cabinet. After removing items for one patient, the caregiver can input patient identification information for another patient into the cabinet and immediately begin removing items for the second patient without waiting for completion of a scanning process, e.g., another 5-30 seconds.

In one embodiment, this is accomplished by using an RFID cabinet configuration having multiple RFID readers integrated into the cabinet. One reader (or set of readers) and its connected antennae is dedicated for inventory management purposes. For example, the antennae for this reader(s) is specifically configured to read all areas of the cabinet with a high degree of accuracy. In this way, all of the items may be periodically scanned at the same time. For instance, this reader(s) could be set to run a full cabinet scan at scheduled intervals. In one aspect, this reader(s) could be triggered to run a full cabinet scan every time the cabinet door is closed. However, it will be appreciated that scans are not limited to occurring only after the door is closed. For example, scans can occur at times of non-use of the cabinet so that the user does not need to wait for a full scan after closing the door before removing additional items. The reader(s) could also be configured to be disabled and any active scans to be paused or terminated when the cabinet is open. In this way, a full inventory scan would only happen when the door is closed and the system is not being utilized (and at periodic intervals).

A second RFID reader (or readers) and its connected antennae may be dedicated for the capture of item transaction information, such as, for example, item removal or restocking. For instance, the antennae for this reader(s) may be specifically configured to read tags in motion as they are removed or returned to the cabinet or storage location. In one aspect, the second reader is enabled only when the cabinet doors are open. The second reader is then disabled when the cabinet door(s) are closed. This permits the scanning of items as they are being removed or replaced (and without scanning all of the other items within the cabinet or storage location). This provides near-real time data to the cabinet computer system (or other associate computer system, such as a back-end computer system operating over a network) which maintains a database of item inventory and location. Also, a display screen on the cabinet could display the transactions to the end-user as the item is being removed or returned. For example, the display screen on the cabinet could recite that: "One syringe is being removed." Another feature of the second RFID reader is that it could be configured to sense direction of movement of an item. In this way, the RFID reader could detect whether an item is being removed or returned.

As previously described, the RFID systems may be used in connection with cabinets, carts, or storage locations. As one example, the cabinet may have a locking door, or multiple individually controlled locking doors. As another example, the invention may provide a room (or multiple rooms) with an electronically controlled lock. The cabinet, cart, or room may contain multiple quantities of multiple items.

The RFID systems, including readers (or multiple readers) are placed within the interior of the cabinet. One of the RFID readers provides continuous monitoring of the items within the cabinet, e.g. identifying the data embedded on the tag of each product. This RFID reader is capable of repeatedly scanning all products in a short time period. A separate reader is responsible for determining when an item has been removed. Since the scanning time period for reading the tag being removed is short, the invention provides alerts prior to the user leaving the vicinity of the cabinet and the controlling computer.

The data associated with the RFID tag may take many forms. In one example, the invention uses a fixed identification (ID) number that is unique to the universe of tags used for all time. At an appropriate point in time, either at the cabinet or a separate workstation or system in central supply, this unique number is read into a database. Other data regarding the product is also entered into the database for subsequent retrieval. This data may include the item type ID, the item unique product number (UPN), expiration date, serial number, manufacturer or other parameters.

In another example, the RFID tags are WORM (write-once, read many) tags. In the case of a WORM tag, some or all of the data may be written once on the readable memory of the tag and thus can be read directly off the RFID tag. If the central database is unavailable, the product can still be identified. In addition, if access to the central server is unavailable, any user alerts given at the time of removal can be made by the local computer and cabinet system.

In yet another example, the RFID tag utilizes a writable tag. For a writable tag, information may be added to the product by the user. For example, the writable tag may contain information selected by the user such as the ID of the patient, the user ID, the date and time of removal, and the like. In all cases, the data formats associated with the tags should be compatible with the software systems, so that accurate reporting down to the item-level detail can be automated.

The types of cabinets and RFID readers that may be used include those described in U.S. Pat. No. 7,348,884, the complete disclosure of which is herein incorporated by reference. The details of how to construct a cabinet that permits scanning of all items stored within the cabinet is described herein.

In order to scan items as they are being removed or returned, the computer system may detect when the door is opened. Upon opening of the door, any scanning of all of the items by a first static RFID reader (or readers) is ceased or prevented. A second transaction reader (or readers) is then activated and used to scan an item or items as they are removed or returned. This reduces the time to record removal or replacement since only the item being removed or replaced is being scanned. The computer system may then update the database containing the inventory of items by adding or subtracting the item or items removed as detected by the second RFID reader. When the door closes, the first RFID reader may then perform its normal scan of all items to confirm the accuracy of the database.

FIG. 1 illustrates one example of a RFID inventory management system incorporated into a cabinet 100 in accordance with the present invention. Although shown here implemented into cabinet 100, the RFID inventory management system as described herein may be integrated into storage carts, other hospital locations, and any other access-controlled areas. Examples of other types of carts and cabinets that may be modified to include the features described herein are described in the following U.S. Patents and patent applications, the contents of which are hereby incorporated by reference: U.S. Pat. No. 6,272,394, issued on Aug. 7, 2001 to Lipps, U.S. Pat. No. 6,385,505, issued on May 7, 2002 to Lipps, U.S. Pat. No. 6,760,643, issued on Jul. 6, 2004 to Lipps, U.S. Pat. No. 5,805,455, issued on Sep. 8, 1998 to Lipps, U.S. Pat. No. 6,609,047, issued on August 19, 2003 to Lipps, U.S. Pat. No. 5,805,456, issued on Sep. 8, 1998 to Higham et al, U.S. Pat. No. 5,745,366, issued on Apr. 28, 1998 to Higham et al., an U.S. Pat. No. 5,905,653, issued on May 18, 1999 to Higham et al., U.S. Pat. No. 5,927,540, issued on Jul. 27, 1999 to Godlewski, U.S. Pat. No. 6,039,467, issued on Mar. 21, 2000 to Holmes, U.S. Pat. No. 6,640,159, issued on Oct. 28, 2003 to Holmes et al., U.S. Pat. No. 6,151,536, issued on Nov. 21, 2000 to Arnold et al., U.S. Pat. No. 5,377,864, issued on Jan. 3, 1995 to Blechl et al., U.S. Pat. No. 5,190,185, issued on Mar. 2, 1993 to Blechl, U.S. Pat. No. 6,975,922, issued on Dec. 13, 2005 to Duncan et al., U.S. Pat. No. 7,571,024, issued on Aug. 4, 2009 to Duncan et al., U.S. Pat. No. 7,835,819, issued on Nov. 16, 2010 to Duncan et al., U.S. Pat. No. 6,011,999, issued on Jan. 4, 2000 to Holmes, U.S. Pat. No. 7,348,884, issued on Mar. 25, 2008 to Higham, U.S. Pat. No. 7,675,421, issued on Mar. 9, 2010 to Higham, U.S. Pat. No. 6,170,929, issued on Jan. 9, 2001 to Wilson et al., U.S. Patent Application Publication No. 2008/0319579 of Vahlberg et al., published on Dec. 25, 2008, and U.S. Patent Application Publication No. 2010/0042437 of Levy et al., published on Feb. 18, 2010.

Cabinet 100 includes a housing frame with locking doors 102. The cabinet 100 and/or doors 102 can be made of a transparent material to allow a user to see items stored within the cabinet 100. Additionally, the cabinet 100 and/or doors 102 can include a (metal) mesh or other material to prevent the radio frequency from a RFID transmitter from propagating outside the cabinet 100. Techniques for shielding RF signals are described in U.S. Pat. No. 7,348,884, the entire contents of which are herein incorporated by reference. The doors 102 can provide access to one or more storage areas 104. These storage areas 104 may be separated by dividers, shelves, drawers, bins and the like. Cabinet 100 may further include one or more static RFID readers 106. Static RFID readers 106 are configured to conduct a scan of the items held within the cabinet 100 while the doors 102 are closed. The static RFID readers 106 can be used to assist in determining the inventory of items within cabinet 100 (or a set of cabinets and/or other access-controlled areas). Cabinet 100 may be linked to a central server via a computer system 110 having at least one processor, memory and computer code to control operation of the various systems associated with cabinet 100 (such as the scanners, door locks, light indicators, and the like). A database of the computer system 110 may be updated with the inventory of items. A central server, or other remotely located computer system, may also receive the updated inventory information from computer system 110 via a computer network. In this way, the data from multiple cabinets located within a healthcare facility may be updated with inventory information in real time. Additionally, cabinet 100 can include one or more transaction RFID readers 108. Transaction RFID readers 108 are configured to operate (from signals received from computer system 110) when one or more of doors 102 is opened to scan items being removed from or placed within the cabinet 100. The transaction RFID readers 108 can be configured to detect moving items that are removed from or placed within the cabinet. Accordingly, transaction RFID readers 108 may be appropriately positioned relative to doors 102 so that they can perform their scan when the door 102 is opened and an item is being removed from or placed into the interior of the cabinet. Information relating to the removal or placement of such items can be stored in or compared with the database using the computer system 110 (and also transmitted to a remote computer system). The detection and storage process of an individual item can take less than about two seconds, allowing for minimal to no delay for a busy clinician. The transactions involving the item may be recorded in and/or checked against the database.

In some embodiments, the cabinet 100 may include an external reader 116. The external reader 116 may be positioned on an exterior of the cabinet 100, such as near the computer system 110 for easy entry of data relating to the transaction involving the item. The external reader 116 may be a bar code scanner, RFID scanner, any other reader configured to identify an item, or a combination of such readers and scanners. External reader 116 can be used when removing items from the cabinet 100 or when placing items in to the cabinet 100. In some cases, the external reader 116 can be used instead of transaction RFID readers 108. For example, the external reader 116 may be used if the transaction RFID readers 108 are broken or disabled, if an item does not include an RFID tag, or if the RFID tag has fallen off or been removed. In some cases, the transaction RFID reader 108 may be used in conjunction with external reader 116, for example, as a quality assurance check. It will be appreciated that any number of doors 102 may be used in cabinet 100, and each of the doors may provide access to one or more shelves, compartments, or other storage areas 104 in which items may be stored. The use of multiple doors 102 and storage areas 104 creates separate areas of access, which may be useful in some applications, such as applications where certain items may only be accessed by users of a particular access level. For example, access zones A1 and A2 can have a different access level than access zone B. Any number of access zones may be created using independently lockable doors 102.

Cabinet 100 may include a guiding light or other indicator signal to locate a correct cabinet 100, door 102, and/or a storage area 104 of the item. Use of guiding lights is described in U.S. Pat. Nos. 5,745,366, 5,805,455, 5,805,456, 6039,467, 6,272,394, and 5,385,505 incorporated herein by reference for all purposes.

Computer system 110 may be embedded into or formed with the cabinet 100, in close proximity to the cabinet 100, or mounted on the cabinet 100. Here, computer system 110 is mounted atop cabinet 100 and is hard wired to the various electrical components of cabinet 100. The computer system 110 may alternatively be coupled with the cabinet 100 (including the various electrical components in cabinet 100) by Ethernet, optical infra-red, serial cable, USB, Bluetooth, other wireless communication interface, or any other data connection means. By using an external computer, either in close proximity with the cabinet 100 or mounted on cabinet 100, the use of a general-purpose computer is possible with varying form factors. For example, the type, size, shape, and/or configuration of the external computer are unconstrained by the cabinet design. The use of such a computer can allow an existing cabinet to be retrofitted with a general computer and/or one or more RFID sensors to achieve the desired efficiency of item tracking. As software rapidly evolves for the RFID cabinet inventory management system control, newer versions often need a new operating system and these in turn need a new computer. By keeping the computer system 110 external, upgrading both software and computer hardware is both easy and inexpensive.

Computer system 110 can include a console screen 114 and an input area 112. For example, input area 112 can include a keyboard, numerical pad, a touchscreen, and the like. In some embodiments, input area 110 can be used to identify a user. For example, a user may input a user ID, password, PIN, and/or other identifier into the input area 112 to validate or authenticate the user's identity to grant access. In some embodiments, a RFID badge, mag card, or other identification device can provide access to the RFID inventory management system. In other embodiments, the input area 112 can include biometric sensors, such as fingerprint, facial, or retinal scanners to identify a user biometrically. Some embodiments may incorporate a wireless device that can be worn or held by a user or otherwise kept in close proximity with the user. The wireless device communicates wirelessly with the computer system 110 to identify a user as the user approaches the cabinet 100. The input area 112 may also be used to select from a variety of options related to the items within the cabinet 100. For example, a user may select an item name or identifier of an item to be removed or replaced, a patient name or ID can be entered into the computer system 110 via the input area 112, and/or a goal for the item may be entered into a record on the computer system 110. For example, goals may include patient use, transfer from a first location to a second location, transforming goods into new forms/assemblies, and waste.

Computer system 110 may further be configured to lock and unlock the doors 102. For example, computer system 110 can unlock and/or open at least one door 102 upon the input of a valid user ID, password, item request, and the like. Each of the doors 102 may be lockable independent from the doors 102 such that only access into selected/allowed areas is enabled. This allows for different storage areas 104 to have different levels of access.

In some embodiments, an expiration date for one or more of the items may be linked to RFID tags. As the first RFID system scans the cabinet, it can be determined whether any of the items in the cabinet have expired or are approaching an expiration date. The computer system can be configured to provide an alert or other indication that such items need to be used prior to expiration or removed from the cabinet after the items have expired.

FIG. 2 illustrates a method for using a RFID inventory management system integrated into a cabinet system, such as cabinet 100 described above. It will be appreciated that a similar method may be used in conjunction with RFID inventory management systems incorporated into carts, other medical locations, and other access-controlled areas. At block 200, a user of the system may be identified. In some embodiments, the user may be identified using a biometric identifier, a password entered into a computer system, and/or using a wireless device that communicates with the computer system when the user is in close proximity with the system to provide the user with access to the cabinet's interior. The user may select a goal or use for the item to be removed from or placed within the cart at block 202. For example, a user may input a goal by keying the goal into the computer, selecting a goal from a list or menu on the computer, or can scan a customer ID, such as by scanning a patient wristband. Goals can include, but are not limited to, patient use, transferring an item from one location to another location, transforming one or more items into a new form and/or assembly, and waste. Goals typically include removing an item from the cart or placing an item into the cart. If a goal is not selected by a user, the system may perform tasks unrelated to physical inventory at block 228. For example, the system may lock the doors of the cart at block 230, activate internal RFID scanners at block 232, and/or put the external motion sensors in a "sleep" mode at block 234.

If a user does select a goal, the system may do one or more tasks related to physical inventory. For example, the system may unlock a specific door to allow access to a selected item or items at block 204, the system may put the internal static RFID scanners into a "sleep" mode or otherwise disable the static RFID scanners at block 206, and/or the system may activate motion sensors (transaction RFID scanners) and/or external static RFID scanners at block 208. The system determines whether the goal involves removing an item or placing an item into the cart at block 210. When the goal involves placing an item into the cart instead of removing an item, an external scan may be conducted at block 212 and/or an auto-removal scan can occur at block 214 as the user places the item into the cart at block 216. As used herein, "auto-removal scan" can refer to both a scan of an item being placed into the cart and to a scan of an item being removed from the cart. The user may be prompted to select whether an external scan of the item is desired, or the external scanner may be active should the user desire to externally scan the item. For example, a bar code may be scanned, a UPN may be entered, the item's RFID tag can be externally scanned, or any other method of identifying the item may be used. The auto-removal scan can be done by using the transaction RFID scanners to sense objects being moved into and out of the cart by the user. Oftentimes, a user will only have either the external scan or the auto-removal scan carried out for a particular application. For example, a user may rely on the transaction RFID scanners to detect items removed from and placed within the cart for inventory management purposes at most times. In some instances, the external scanner may be used to track items that do not contain RFID tags or can be used if the transaction RFID scanners are broken, disabled, or otherwise inactive. In some cases, both the external scan and the auto-removal scan may be used together, such as for quality assurance checks. After an auto-removal scan has been conducted or skipped the system may prompt the user to select whether a second item is required for the goal at block 224. If the user needs a second item for the goal, the system can determine whether an item is to be removed from the cart or is to be placed in the cart at block 220. The system may automatically determine if a second item is required based on the selected goal. When there is not an extra item required for the goal, the user may be asked to select whether the user has a new goal at block 226. If the user has a new goal, the user may then select a goal at block 202. If the user does not have a second goal, the system may lock the doors at block 230, activate the internal static RFID scanners at block 232, and/or set the external motion sensors (transaction RFID scanners) to "sleep" mode at block 234. The system can then update an inventory database using the inventory as detected by the static RFID sensors at block 236. The system can then be accessed by a new user or the same user at a later time by returning to block 200.

In cases where an initially selected goal involves removing an item from the cart, the item may be selected and removed by a user at block 218. An auto-removal scan may be conducted at block 220 as the user removes the item at block 222. The user then has the option of conducting an external scan of the item. As described above, either one or both of the auto-removal scan and the external scan can be conducted based on the user's preferences. After the item has been scanned, the system may prompt the user to select whether a second item is required for the goal at block 224 and the process may continue as described above.

During the scanning by the transaction RFID scanners and/or the static RFID scanners, the particular transaction can be stored in and/or checked against the database. In some embodiments, the selected goal may be entered by an external scan of an item. The computer may be configured to recognize this scan as a goal to place the item into the cabinet. The computer can then unlock one or more doors, put the internal static RFID sensors in "sleep" mode, activate motion sensors (transaction RFID scanners). An auto-removal scan may be conducted as the item is placed within the cabinet. The system can continue to the inventory process as described above for the placement of an item within the cart.

The use of both static and dynamic (transaction) RFID scanners allows users to efficiently retrieve items from a cart while maintaining accurate inventory. The static scanner(s) can conduct periodic scans of all of the items in the cabinet, such as scans conducted when the doors are closed, to maintain an inventory of all of the items. Because all or substantially all of the items are scanned at this time, the scan may take from 5-30 seconds. To ensure that a user does not experience this delay when an item is needed, dynamic scanners may be activated when the doors are opened. The dynamic scanners can then detect removal of items from or placement of items within the cabinet. As only the removed and/or placed items are scanned, the time required for the scan can be less than about 2 seconds. Reducing this delay can be particularly advantageous when a caregiver is removing items for multiple patients. After removing items for one patient, the caregiver can input patient identification information for another patient into the cabinet and immediately begin removing items for the second patient without waiting for completion of a full inventory scanning process, e.g., another 5-30 seconds.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known, processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

The invention has now been described in detail for purposes of clarity and understanding. However, it will be appreciated that certain changes and modifications may be practiced within the scope of the appended claims.

What is claimed is:

1. A cabinet system for monitoring items having an RFID tag, the system comprising:
   a cabinet comprising:
      an interior where items are stored, wherein the cabinet is divided into at least two zones, and wherein each zone has a different access level; and
      at least one door providing direct access to each of the zones to gain access to at least some of the items via an opening that is covered by the doors when the doors are closed;
   a static RFID system for reading and identifying data embedded on RFID tags located on at least some of the items placed within the cabinet, wherein the static RFID system is configured to scan substantially all of the items located within the zones of the cabinet when the doors are closed;
   a transaction RFID system for reading the data on one of the RFID tags upon detecting removal of the associated item from the RFID cabinet, wherein the transaction RFID system is positioned on the cabinet such that when an item is removed from the interior, the item must pass through the transaction RFID system to permit the item to be detected and scanned while being removed from the interior through the opening without scanning other items in the cabinet; and
   a computer system that is configured to receive an input that identifies a user, and wherein the computer system is configured to periodically record the data read from the RFID tags by the static RFID system and the transaction RFID system.

2. The cabinet system according to claim 1, wherein the computer system is configured to detect opening and closing of the doors, and wherein the transaction RFID system is activated by one of the doors being opened and is deactivated by one of the doors being closed.

3. The cabinet system according to claim 2, wherein each of the plurality of zones comprises a different level of access.

4. The cabinet system according to claim 1, wherein the transaction RFID system is configured to read the data on one of the RFID tags for a detection time that is less than 2 seconds while the static RFID system requires at least 5 seconds to scan substantially all of the items.

5. The cabinet system according to claim 1, wherein the computer system is configured to store and correlate expiration date information with the items in the cabinet and to provide an indication of an approaching or past expiration date for each of the items.

6. The cabinet system according to claim 1, wherein the input comprises one or more of a biometric identifier, a username, a password, and a signal from a wireless device assigned to the user.

7. The cabinet system according to claim 1, further comprising an external item reader, the external item reader comprising at least one of a RFID scanner and a bar code reader.

8. The cabinet system according to claim 1, wherein the static RFID system is configured to be placed in sleep mode where items are not scanned when the door is open and the transaction RFID system is active.

9. A cabinet system for monitoring items having an RFID tag, the system comprising:
   a cabinet comprising:
      a frame;
      a computer system supported by the frame and having a display screen;
      an interior where items are stored; and
      at least one door providing direct access to at least some of the items via an opening that is covered by the at least one door when the at least one door is closed;

a static RFID system for reading and identifying data embedded on RFID tags located on at least some of the items placed within the cabinet, wherein the static RFID system is configured to scan substantially all of the items located within a specified portion of the interior of the cabinet when the at least one door is closed;

a transaction RFID system separate from the static RFID system for reading the data on one of the RFID tags upon removal of the associated item from the RFID cabinet without reading the data on the other RFID tags remaining in the cabinet;

wherein the computer system is configured to display on the display screen a name of the item that has been removed;

wherein the computer system is configured to receive an input that identifies a user, and wherein the computer system is configured to periodically record the data read from the RFID tags by the static RFID system and the transaction RFID system.

10. The cabinet system according to claim 9, wherein the cabinet further comprises a plurality of doors and the interior comprises a plurality of storage areas, and wherein each of the plurality of doors controls access to a corresponding one of the plurality of storage areas.

11. The cabinet system according to claim 10, wherein each of the plurality of storage areas comprises a different level of access.

12. The cabinet system according to claim 9, wherein the transaction RFID system is configured to read the data on one of the RFID tags for a detection time that is less than 2 seconds while the static RFID system requires at least 5 seconds to scan substantially all of the items.

13. The cabinet system according to claim 9, wherein the computer system is configured to store and correlate expiration date information with the items in the cabinet and to provide an indication of an approaching or past expiration date for each of the items.

14. The cabinet system according to claim 9, wherein the input comprises one or more of a biometric identifier, a username, a password, and a signal from a wireless device assigned to the user.

15. The cabinet system according to claim 9, further comprising an external item reader, the external item reader comprising at least one of a RFID scanner and a bar code reader.

16. The cabinet system according to claim 9, wherein the static RFID system is configured to be placed in sleep mode where items are not scanned when the door is open and the transaction RFID system is active.

17. A cabinet system for monitoring items having an RFID tag, the system comprising:
a cabinet comprising:
an interior where items are stored; and
at least one door providing direct access to at least some of the items via an opening that is covered by the at least one door when the at least one door is closed;
a static RFID system for reading and identifying data embedded on RFID tags located on at least some of the items placed within the cabinet, wherein the static RFID system is configured to scan substantially all of the items located within a specified location in the interior of the cabinet when the at least one door is closed;
a transaction RFID system for reading the data on one of the RFID tags upon detecting removal of the associated item from the RFID cabinet, wherein the transaction RFID system is activated by the at least one door being opened and is deactivated by the at least one door being closed, and wherein the transaction RFID system is positioned on the cabinet such that when an item is removed from the interior, the item must pass through the transaction RFID system to permit the item to be detected and scanned while being removed from the interior through the opening without scanning other items in the cabinet; and
a computer system that is configured to detect opening and closing of the at least one door, wherein the computer system is configured to stop or pause any reading of the data of the RFID tags by the static RFID system upon detection of the door opening,
wherein the computer system is further configured to receive an input that identifies a user, and wherein the computer system is configured to periodically record the data read from the RFID tags by the static RFID system and the transaction RFID system.

18. The cabinet system according to claim 17, wherein the transaction RFID system is configured to read the data on one of the RFID tags for a detection time that is less than 2 seconds while the static RFID system requires at least 5 seconds to scan substantially all of the items.

19. The cabinet system according to claim 17, wherein the computer system is configured to store and correlate expiration date information with the items in the cabinet and to provide an indication of an approaching or past expiration date for each of the items.

20. The cabinet system according to claim 17, wherein the input comprises one or more of a biometric identifier, a username, a password, and a signal from a wireless device assigned to the user.

* * * * *